United States Patent [19]

Alderman

[11] Patent Number: 4,695,464

[45] Date of Patent: Sep. 22, 1987

[54] SUSTAINED RELEASE DOSAGE FORM BASED ON HIGHLY PLASTICIZED CELLULOSE ETHER GELS

[75] Inventor: Daniel A. Alderman, Midland, Mich.

[73] Assignee: The Dow Chemical Company, Midland, Mich.

[21] Appl. No.: 658,965

[22] Filed: Oct. 9, 1984

[51] Int. Cl.$^4$ .......................... A61K 9/02; A61K 9/20
[52] U.S. Cl. .................................. 424/449; 514/781; 604/896; 604/897
[58] Field of Search .......................... 424/19, 28, 449; 604/896, 897; 514/781

[56] References Cited

U.S. PATENT DOCUMENTS

| 3,065,143 | 11/1962 | Christensen et al. | 424/35 |
|---|---|---|---|
| 4,140,756 | 2/1979 | Gallian | 424/19 |
| 4,155,993 | 5/1979 | Belleville | 424/19 |
| 4,259,314 | 3/1981 | Lowery | 424/19 |
| 4,369,172 | 1/1983 | Schor et al. | 424/19 |
| 4,528,125 | 7/1985 | Alderman et al. | 252/522 A |

FOREIGN PATENT DOCUMENTS 58-59910 4/1983 Japan.
59-216822 12/1984 Japan.

OTHER PUBLICATIONS

PDR 1984 38th Ed pp. 875, 1834.

Primary Examiner—Ronald W. Griffin

[57] ABSTRACT

A transdermal pharmaceutical dosage form comprises
(1) a gel matrix comprising a water-soluble cellulose ether homogeneously dispersed in a major amount of the weight of said gel matrix of a plasticizer for said cellulose ether, said gel matrix having dispersed therein a pharmaceutically active agent;
(2) a non-porous covering and
(3) means for adhering the dosage to the skin of a human or animal patient.

8 Claims, 2 Drawing Figures

SECTION A-A

SUSTAINED RELEASE DOSAGE FORM BASED ON HIGHLY PLASTICIZED CELLULOSE ETHER GELS

BACKGROUND OF THE INVENTION

This invention relates to a sustained release pharmaceutical dosage form, more particularly to a thermoplastic water-soluble transdermal dosage form for the sustained release of pharmaceuticals.

The object of much research in recent years has been to provide sustained release dosage forms for pharmaceuticals. Most pharmaceuticals have a rather narrow therapeutic range in which they are of optimum benefit. Above or below this range, the drug is ineffective and/or toxic. In administering a tablet or capsule of the drug, the concentration thereof in the body may at first exceed therapeutic levels. Drug concentration then gradually decreases with time, until it falls below the therapeutic range. Thus, the time during which the drug is present in effective amounts may be quite short.

Sustained release or controlled release dosage forms are of interest because they can deliver and maintain optimum therapeutic levels of a medicament for a longer period of time than a conventional dosage form. In addition, such dosage forms can often deliver the medicament without an initial release of a greater than a therapeutic amount thereof. An additional advantage is that by using a sustained release form, it is often possible to increase the time between successive administrations of the medicament, in effect reducing the frequency of administration.

Various sustained release dosage forms have been developed using cellulose ethers as a release controlling component. In U.S. Pat. No. 3,065,142 to Christiansen et al. it is taught to prepare a compressed matrix from a mixture of a powder methylcellulose or hydroxypropyl methylcellulose and an active medicament. Similar technology is also disclosed in U.S. Pat. Nos. 4,369,172 and 4,389,393. This dosage form has found great utility as an oral dosage form, a rectal suppository or intravaginal device. Unfortunately, however, these dosage forms have some properties which tend to limit their utility. For example, such dosage forms sometimes provide a high initial release of medicament which may in some instances be undesirable. Moreover, since the matrices in these dosage forms are not thermoplastic, the shape of such dosage forms is limited to those which can be prepared by compressing powdered cellulose ethers.

It is also known to make a sustained release dosage form by coating a pharmaceutical with a water-insoluble cellulose ether such as ethylcellulose, cellulose acetate phthalate, and the like. This approach has also been found to be useful in certain instances but the coating process employed is expensive and the shape and manner of use of the product dosage form are limited.

European Patent Publication No. 0050480 discloses a multiple layer sustained release dosage form for the delivery of prostaglandin. Such dosage form comprises outer release controlling layers of hydroxypropyl cellulose (HPC), a water-insoluble polymer such as polyvinyl acetate or cellulose acetate, and a minor amount of a plasticizer. This added release controlling layer optionally, but less preferably, contains a prostaglandin. This dosage form further contains a drug storing layer comprising a water-soluble polymer such as HPC, a prostaglandin and optionally a minor amount of a plasticizer in a water-insoluble polymer. In this system, the presence of a water-insoluble polymer is considered essential to provide controlled release of the prostaglandin.

Similarly, in European Patent Publication No. 0086093 there is disclosed a three-layer pharmaceutical dosage form. This form comprises outer layers of HPC and a minor amount of a plasticizer (optionally containing prostaglandin) and a middle drug storing layer comprised of a water-insoluble polymer, a water-soluble polymer such as polyvinylpyrrolidone or HPC, plasticizer and an organic acid. In this reference, the use of a water-insoluble polymer is considered necessary in order to provide a suitable sustained release dosage form. Moreover, this dosage form requires the formation of the respective film layers followed by lamination of the layers to form the final product. In addition, this dosage form is not said to be useful as other than a prostaglandin delivery system.

Another limitation of the foregoing dosage forms is that they are not useful as internal dosage forms such as tablets, suppositories, intravaginal devices, and the like. More recently, the use of transdermal delivery systems to deliver pharmaceuticals over an extended period has been developed. Most such systems employ a membrane at the diffusion controlling layer, in conjunction with a separate drug storing layer. Although transdermal delivery systems are becoming accepted as a means to administer a drug, it would be desirable to provide a transdermal system which is simple and inexpensive to manufacture.

In view of the deficiencies of the previously known sustained release forms, it would be desirable to provide an inexpensive, easily prepared, transdermal pharmaceutical dosage form which is widely applicable to diverse modes of pharmaceutical administration.

SUMMARY OF THE INVENTION

The present invention is a dosage form for the transdermal release of a pharmaceutically active agent. The dosage form of this invention comprises (1) a thermoplastic water-soluble gel matrix comprising a water-soluble cellulose ether homogeneously dispersed in a major amount of the weight of said gel matrix of a plasticizer for said cellulose ether, said gel matrix having dispersed therein a pharmaceutically active agent; (2) a non-porous covering attached to said gel matrix such that the gel matrix is exposed only on one side, and (3) a means for adhering the dosage form to human or animal skin such that exposed surface of the gel matrix is in contact with the patient's skin without exposure thereof to the air.

In another aspect, this invention is a transdermal pharmaceutical dosage form comprising (1) a thermoplastic water-soluble gel matrix comprising a water-soluble cellulose ether homogeneously dispersed in a major amount of the weight of said gel matrix of a plasticizer for said cellulose ether, said gel matrix having dispersed therein a pharmaceutically active agent;

(2) a non-porous covering, covering the gel matrix so that the gel matrix is exposed only on one side, and (3) a means for adhering the dosage form to human or animal skin such that the exposed surface of the gel matrix is in contact with the skin without exposure to the air.

This dosage form provides for excellent transdermal release of the drug contained therein, without releasing an initial high concentration of drug. Because the gel matrix acts as both drug reservoir and diffusion-controlling mechanism, the dosage form is more economically and simply manufactured than conventional transdermal delivery devices.

DETAILED DESCRIPTION OF THE INVENTION

Figure 1:
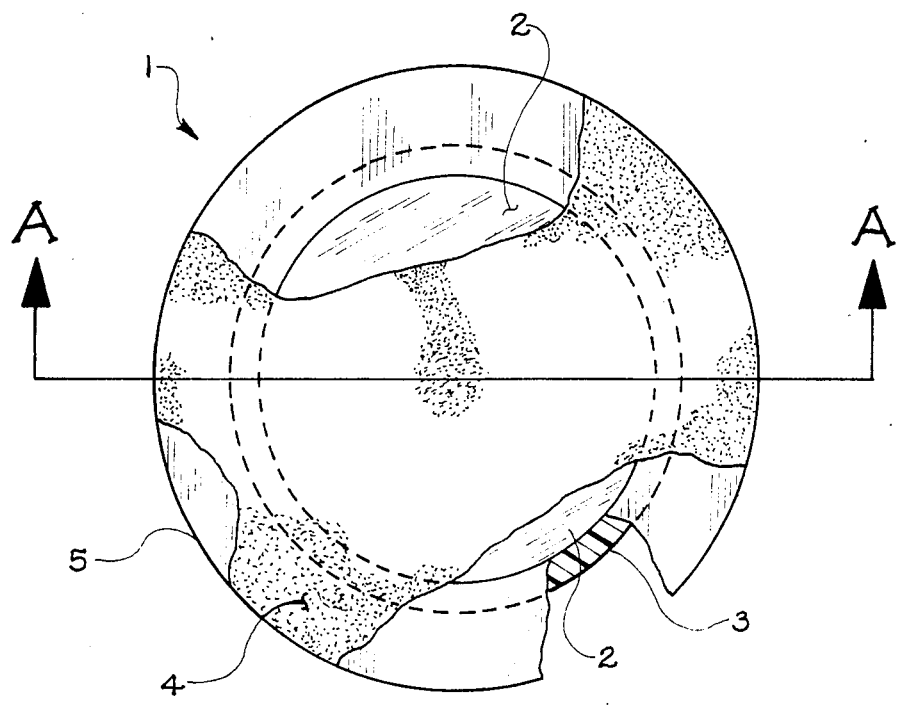
FIG. 1 is a bottom view, partially in section, of an embodiment of the dosage form of this invention.

The dosage form of this invention comprises, as one component, a thermoplastic water-soluble gel matrix comprising a water-soluble HPMC homogeneously dispersed into a major amount of a plasticizer, into which gel matrix is dispersed a pharmaceutically active agent (drug).

The HPMC used herein contains sufficient hydroxypropoxyl and methoxyl substitution to render it water-soluble. HPMC having a methoxy degree of substitution from about 0.8 to about 2.5 and a hydroxypropoxyl molar substitution from about 0.05 to about 3.0 are generally water-soluble. "Methoxy degree of substitution" (MDS) refers to the average number of methyl ether groups present per anhydroglucose unit of the cellulose molecule. "Hydroxypropoxyl molar substitution" (HPMS) refers to the average number of moles of propylene oxide which are reacted with each anhydroglucose unit of the cellulose molecule.

The molecular weight of the HPMC used herein is not especially critical as long as the HPMC forms a gel matrix with the plasticizer employed herein. However, the molecular weight of the cellulose ether does affect both the release profile of the dosage form as well as its physical properties. As a general rule, the use of higher molecular weight HPMC causes the dosage form to have greater physical strength and a longer drug release profile. Thus, it is readily seen that the molecular weight of the HPMC is a parameter which is readily manipulated by the practitioner to achieve a desired release profile or physical property in the product dosage form.

The molecular weight of a water-soluble cellulose ether is generally expressed in terms of the viscosity at 20° C. of an aqueous solution containing two percent by weight of the polymer. Suitable HPMC includes those having a viscosity from about 5 to about 100,000 centipoises. To obtain a dosage form providing a relatively fast release of drug and/or moderate physical strength, a HPMC having a viscosity of about 5-15,000, preferably 100-4,000 is suitable. For more prolonged release of drug, and/or greater strength, a HPMC having a viscosity of about 15,000-100,000, preferably 15,000-75,000 is suitable. It should be noted that factors other than the particular HPMC employed also affect these properties. For example, an increasing amount of plasticizers extends to reduce the physical strength of the dosage form and increases the rate of drug release.

Since the dosage form is used in contact with the skin, the HPMC must be non-irritating, although it is preferred that the HPMC be of a purity suitable for consumption.

Preferred HPMC includes those having a MDs from about 1.8 to 2.0 and HPMS from about 0.2 to about 0.31 such as is commonly available under the trade names Methocel® E Premium and Metalose® 60SH; those having a MDS from about 1.1 to about 1.6 and a HPMS of 0.1 to 0.3 such as are commercially available under the tradenames Methocel® K Premium and Metalose® 90SH; and those having a MDS from about 1.1 to 1.5 and a HPMS from about 0.7 to 1.0 such as are commercially available under the tradename Methocel® J. Methocel products are available from The Dow Chemical Company and Metalose products are available from Shin-etsu Chemical Company, Ltd. Japan.

The gel matrix further comprises a plasticizer for the HPMC. The plasticizer employed herein is a material which (a) reduces the softening point of the HPMC below its decomposition temperature and desirably (b) imparts more desirable physical properties to the gel matrix. A further characteristic of the plasticizer is that it is compatible with the HPMC at the relative proportions thereof present in the dosage form. By "compatible" it is meant that a substantially homogeneous dispersion or solution of the HPMC in the plasticizer is made with little or no tendency for the HPMC and plasticizer to phase separate.

Preferably, the plasticizer employed herein is also a solvent for the HPMC at the elevated temperature at which the dosage form is prepared. Such plasticizer, when mixed with the HPMC above a characteristic temperature at which the HPMC becomes soluble therein, dissolves the HPMC. Upon cooling, the mixture forms a gel matrix having especially useful properties for use in a sustained release dosage form.

Suitable plasticizers include low molecular weight polyols having aliphatic hydroxyls such as ethylene glycol, propylene glycol, 1,2-butylene glycol, 2,3-butylene glycol, styrene glycol, polyethylene glycol such as diethylene glycol, triethylene glycol, tetraethylene glycol and other polyethylene glycols having a molecular weight of about 1,000 or less, polypropylene glycol of molecular weight 200 or less, glycol ethers such as monopropylene glycol, monoisopropyl ether, propylene glycol monoethyl ether, ethylene glycol monoethyl ether, diethylene glycol monoethyl ether, ester-type plasticizers such as sorbitol lactate, ethyl lactate, butyl lactate, ethyl glycolate, allyl glycolate and amines such as monoethanolamine, diethanolamine, triethanolamine, monoisopropanolamine, triethylenetetramine, 2-amino-2-methyl-1,3-propanediol and the like. Of these, the low molecular weight polyethylene glycols, ethylene glycol, low molecular weight polypropylene glycols and especially propylene glycol are preferred.

The plasticizer is employed herein in an amount sufficient to render the dosage form thermoformable. Typically, the plasticizer will comprise a major amount of the weight of the dosage form. Preferably, the plasticizer comprises from about 25 to 95 percent of the combined weight of plasticizer and HPMC. The amount of plasticizer present in the dosage form very substantially affects its properties. A more flexible dosage form is obtained when a relatively high level of plasticizer, i.e., 50-90%, is present in the dosage form. The use of a lesser amount of plasticizer (i.e., 30-50%, preferably 40-50%) provides a stiffer, harder dosage form.

The dosage form of this invention further contains at least one pharmaceutically active agent (drug) which is capable of being released in active form from the gel matrix under the conditions at which the dosage form is used. Preferably, the pharmaceutically active agent is heat stable, that is capable of being heated to a temperature sufficient to prepare a gel matrix from the HPMC and the plasticizer without being rendered pharmaceutically inactive. The drug is also one which acts locally or which may be transmitted in active form through the skin. Thus, the drug must be able to permeate the skin and/or be carried through the skin by a carrier material which is optionally employed in the dosage form of this invention.

Suitable pharmaceutically active agents include antacids, anti-inflammatory substances, coronary vasodilators, cerebral vasodilators, peripheral vasodilators, anti-infectives, psychotopics, antimanics, stimulants, antihistamines, laxatives, decongestents, vitamins, gastrointestinal sedatives, antidiarrheal preparations, antianginal drugs, antiarrhythmics, antihypertensive drugs, vasoconstrictors, migraine treatments, anticoagulants, antithrombotic drugs, analgesics, antipyretics, hypnotics, sedatives, anti-emetics, antinauseants, anticonvulsants, neuromuscular drugs, hyper- and hypoglycaemic agents, thyroid and antithyroid preparations, diuretics, antispasmodics, uterine relaxants, mineral and nutritional additives, antiobesity drugs, anabolic drugs, erythropoietic drugs, antiasthmatics, expectorants, cough suppressants, mucoltics, antiuricemic drugs and other drug substances such as topical analgestics, local anaesthetics and the like.

When the drug does not readily permeate the skin, a carrier material, typically a low molecular weight organic material in which the drug is soluble and which itself readily permeates the skin, may be employed in the gel matrix. Generally, the amount thereof is chosen such that the gel matrix retains its physical integrity.

In addition to the foregoing critical components, various optional ingredients such as are conventionally used in the art, may be employed in the dosage form of this invention. For example, colorings, flavorings, sweeteners, fragrances, diluents, fillers, preservatives, anti-oxidants, stabilizers, lubricants, and the like may be employed herein if desired. Also, a minor amount of additional water-soluble or insoluble polymers, such as hydroxypropyl cellulose, carboxymethylcellulose, methylcellulose, ethylcellulose, polyvinyl pyrrolidones, may optionally be used herein. When such optional polymer is used, it does not exceed about 50% by weight of the weight of the HPMC used herein. The use of such optional polymers are not generally preferred, but may in certain instances be useful in providing a particular rate of drug release.

The gel matrix used in this invention can be prepared by mixing together the HPMC, plasticizer and phamaceutically active agent under conditions sufficient to homogeneously disperse the HPMC into the plasticizer.

As described hereinbefore, the preparation of the dosage form is advantageously conducted at an elevated temperature. When elevated temperatures are used, it is important to select a temperature at which the pharmaceutically active agent is stable, or if a higher temperature is desired to minimize the time during which the drug is exposed to such temperatures in order to minimize degradation of the drug. Mixing is accomplished in conventional manner using any suitable apparatus until the HPMC is homogeneously dispersed into the plasticizer.

As stated hereinbefore, a plasticizer is preferably a material in which the HPMC becomes soluble at elevated temperatures. When such a plasticizer is used, the dosage form is advantageously prepared by conducting the mixing step at a temperature at which the HPMC is soluble in the plasticizer, subject to the limitations described hereinbefore.

Following the mixing of the HPMC, plasticizer and pharmaceutically active agent, the resulting dispersion is cooled to form a dosage form having a gel matrix into which the pharmaceutically active agent is reversibly dispersed.

Attached to the gel matrix is a non-porous covering. This covering covers all sides of the gel matrix except that side which contacts the skin. The function of the covering is primarily to prevent the evaporation and oxidation of the components of the gel matrix, particularly the drug and the plasticizer. The covering is also useful to facilitate handling and prevent contamination, as well as for cosmetic purposes. The covering may be of any non-irritating non-porous material, but is preferably a plastic.

The gel matrix can be attached to the covering by simply pouring the softened gel matrix into the preshaped covering, and then cooling the gel matrix in situ. An adhesive may be employed to further secure the attachment of the gel matrix to the covering, but is not usually necessary. Alternatively, the gel matrix and non-porous covering can be co-extruded, whereby the covering and gel matrix are shaped and joined in a single operation.

The dosage form of this invention further comprises a means for adhering the dosage form to the skin of a patient, such that the exposed gel matrix surface is in contact with the patients skin but not exposed to the air. Various well known adhesives are suitable for this purpose, including, for example, polymeric latexes such as polymers of styrene and butadiene, acrylic polymers and the like. The adhesive means may be applied directly to the surface of the gel matrix if the adhesive does not impede the diffusion of the drug out of the gel matrix and into the skin. Application of an adhesive in this manner is preferred in that more intimate contact between the skin and the gel matrix is achieved. However, the adhesive can be applied only to a portion of the covering which also contacts the skin during use. For example, the portion of the covering adjacent to the exposed edge of the gel matrix may be extended beyond the edge of the gel matrix to form a "lip", rim, or edge which contacts the skin. The adhesive may be attached to the "lip", rim, or edge. Alternatively, the covered gel matrix may be taped onto the patient's skin using conventional adhesive or surgical tape.

Although a separate diffusion-controlling layer is not normally required in the invention, in certain instances such diffusion-controlling layer may be advantageous herein. When employed, such diffusioncontrolling layer is positioned over the exposed surface of the gel matrix. Such diffusion-controlling layer generally comprises a porous polymeric membrane. Any membrane material having to be useful as a drug diffusion-controlling layer can be used herein for that purpose. Polysiloxane and cellulosic membranes are examples of such membranes.

Referring to FIG. 1, the dosage form 1 has a polymeric covering 3 having a cavity containing gel matrix 2. The gel matrix contains a pharmaceutically active agent. The covering 3 has a flat flanged area 5 approximately coplanar with the exposed surface of gel matrix 2. Applied to the flat flanged area 5 is an adhesive 4 for attaching the dosage form to the skin of an animal or human patient. It is noted that the dimensions of the covering 3, cavity, flanged area 5, etc. may vary substantially to fit the administration requirement of any drug.

Figure 2:
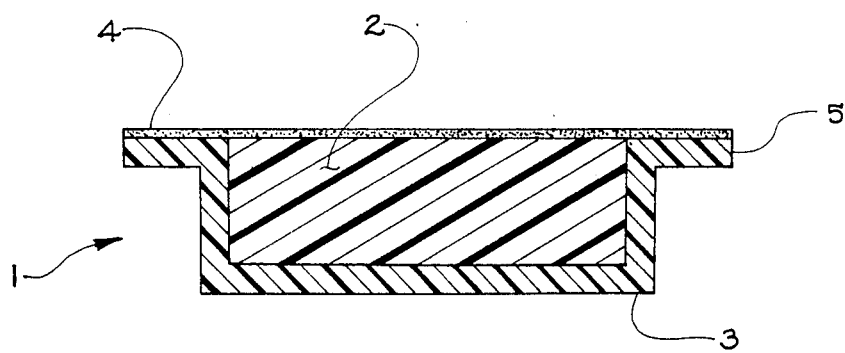
FIG. 2 is a cross-sectional view of the embodiment of this invention illustrated in FIG. 1.

FIG. 2 provides a cross-sectional view of the dosage form showing the cavity in the polymeric covering 3 in which the gel matrix 2 is contained. An adhesive layer 4 is provided on flat flanged area 5 of the polymeric covering. In packaging, a removable covering is advantageously positioned over adhesive layer 4 and gel matrix 2 to prevent contamination thereof.

The dosage form of this invention is useful for the transdermal delivery of a pharmaceutically active agent to a human or animal. The dosage form is used by adhering it to the skin of the patient such that the exposed gel matrix is in intimate contact with the skin. Over a period of hours or even days, the drug diffuses out of the gel matrix and through the skin, due in part to the mixture present at the interface of the skin and gel matrix. The transdermal device is administered until the rate of drug diffusion through the skin is no longer sufficient to maintain a therapeutic level of drug. Often, the dosage form of this invention delivers the drug at a therapeutic level for a period of 1–50, preferably 2–24, more preferably 3–12 hours.

EXAMPLE 1

A gel matrix is prepared by mixing together 25 parts by weight propylene glycol and 75 parts by weight of a HPMC having a MDS of about 1.1 to 1.6, a HPMS of about 0.7–1.0 and a viscosity as a 2% aqueous solution of 5 centipoises. To this mixture are added 5 parts riboflavin. The resulting mixture is stirred briefly and fed into a Haake ¾ inch from zone extruder. The extruder zones are at 120° C., 125° C., 130° C. and 120° C., respectively. During the movement of the mixture through the extender, it becomes more viscous as the temperature rises and the polymer goes into solution. Dissolution of the HPMC into the propylene glycol occurs at about 105° C. The resulting extrudate is a flat ribbon about 1/10 inch thick and 1 inch wide.

A one inch section of the gel matrix is softened and placed into the cavity of a plastic covering having a flanged edge. An adhesive is placed on the flanged edge and the covering containing the gel matrix is fastened to a lightly water-moistened paper towel to simulate the condition of transdermal drug delivery. After a few hours, leaching of the riboflavin through the moistened paper towel is seen. The leaching continues for several days, demonstrating that the drug is gradually released from the gel matrix to a moist porous substrate.

What is claimed is:

1. A transdermal pharmaceutical dosage form comprising
   (1) a thermoplastic water-soluble gel matrix comprising a water-soluble cellulose ether homogeneously dispersed in an amount of a plasticizer for the cellulose ether sufficient to render the dosage form thermoformable, said gel matrix having dispersed therein a pharmaceutically active agent;
   (2) a non-porous covering attached to said gel matrix such that the gel matrix is exposed only on one side, and
   (3) a means for adhering the dosage form to human or animal skin such that exposed surface of the gel matrix is in contact with the skin without exposure to the air.

2. The dosage form of claim 1 wherein said plasticizer is a solvent for said cellulose ether is hydroxypropyl methylcellulose, and the hydroxypropyl methylcellulose at an elevated temperature.

3. The dosage form of claim 2 wherein said hydroxypropyl methylcellulose has a hydroxypropyl molar substitution from about 0.05 to 3.0 and a methoxyl degree of substitution from about 0.8 to 2.5.

4. The dosage form of claim 3 wherein said hydroxypropyl methylcellulose has a hydroxypropyl molar substitution from about 0.2 to 0.31 and a methoxyl degree of substitution from about 1.8 to 2.0.

5. The dosage form of claim 3 wherein said hydroxypropyl methylcellulose has a hydroxypropyl molar substitution from about 0.1 to 0.3 and a methoxyl degree of substitution from about 1.1 to 1.6.

6. The dosage form of claim 3 wherein said hydroxypropyl methylcellulose has a hydroxypropyl molar substitution from about 0.7 to 1.0 and a methoxyl degree of substitution from about 1.1 to 1.6.

7. The dosage form of claim 2 wherein said plasticizer is ethylene glycol, a low molecular weight polyethylene glycol, propylene glycol or a low molecular weight polypropylene glycol.

8. The dosage form of claim 1 further comprising a diffusion-controlling membrane attached to and covering the exposed surface of the gel matrix.

* * * * *